(12) United States Patent
Benesch et al.

(10) Patent No.: US 7,003,149 B2
(45) Date of Patent: Feb. 21, 2006

(54) METHOD AND DEVICE FOR OPTICALLY MONITORING FABRICATION PROCESSES OF FINELY STRUCTURED SURFACES IN A SEMICONDUCTOR PRODUCTION

(75) Inventors: Norbert Benesch, Nürnberg (DE); Claus Schneider, Bubenreuth (DE); Lothar Pfitzner, Erlangen (DE)

(73) Assignees: Semiconductor 300 GmbH & Co. KG, Dresden (DE); Fraunhofer-Gesellschaft zur Foerderung der Angewandten Forschung E. V., Munich (DE)

( * ) Notice: Subject to any disclaimer, the term of this patent is extended or adjusted under 35 U.S.C. 154(b) by 651 days.

(21) Appl. No.: 09/873,230

(22) Filed: Jun. 4, 2001

(65) Prior Publication Data

US 2002/0051564 A1 May 2, 2002

Related U.S. Application Data

(63) Continuation of application No. PCT/EP99/09410, filed on Dec. 2, 1999.

(30) Foreign Application Priority Data

Dec. 4, 1998 (DE) ................. 198 55 983
May 17, 1999 (DE) ................. 199 22 614

(51) Int. Cl.
*G06K 9/00* (2006.01)

(52) U.S. Cl. ............... 382/145; 382/156; 382/159; 382/224; 250/559.01; 356/237.5

(58) Field of Classification Search ............... 382/145, 382/147, 149, 224, 156, 170, 209, 155, 159; 356/237.5; 250/559.09, 559.01
See application file for complete search history.

(56) References Cited

U.S. PATENT DOCUMENTS

| 4,964,726 A | | 10/1990 | Kleinknecht et al. |
| 5,703,692 A | | 12/1997 | McNeil et al. |
| 5,768,192 A | | 6/1998 | Eitan |
| 5,830,611 A | | 11/1998 | Bishop et al. |
| 5,982,921 A | * | 11/1999 | Alumot et al. ............... 382/145 |
| 6,011,725 A | | 1/2000 | Eitan |
| 6,137,570 A | * | 10/2000 | Chuang et al. .......... 356/237.5 |
| 6,191,459 B1 | | 2/2001 | Hofmann et al. |

FOREIGN PATENT DOCUMENTS

DE 198 24 624 A1 2/1999
EP 0 874 396 A2 10/1998

(Continued)

OTHER PUBLICATIONS

M. G. Moharam et al.: "Three-dimensional vector coupled-wave analysis of planar-grating diffraction", *J. Opt. Soc. Am.*, vol. 73, No. 9, Sep. 1983, pp. 1105-1112.

(Continued)

*Primary Examiner*—Bhavesh M. Mehta
*Assistant Examiner*—John Strege (57) ABSTRACT

A method for monitoring fabrication processes of finely structured surfaces in a semiconductor fabrication includes the steps of providing reference signatures of finely structured surfaces, measuring at least one signature of a test specimen surface, comparing the measured signature with the reference signatures, and classifying the test specimen surface by using the comparison results, wherein the measurement of the reference signatures is carried out by measuring the local distribution and/or intensity distribution of diffraction images on production prototypes having a specified quality. The classification is preferably carried out here with a neural network having a learning capability and/or a fuzzy logic. Furthermore, a device for carrying out the method is provided.

26 Claims, 7 Drawing Sheets

FOREIGN PATENT DOCUMENTS

| JP | 60 224 041 | 11/1985 |
|----|------------|---------|
| JP | 61 169 750 | 7/1986 |
| JP | 62 200 251 | 9/1987 |
| JP | 9 191 032 | 7/1997 |
| JP | 9 318 330 | 12/1997 |

OTHER PUBLICATIONS

M. G. Moharam et al.: "Rigorous coupled-wave analysis of metallic surface-relief gratings", *J. Opt. Soc. Am. A*, vol. 3, No. 11, Nov. 1986, pp. 1780-1787.

S. S. H. Naqvi et al.: "Etch depth estimation of large-period silicon gratings with multivariate calibration of rigorously simulated diffraction profiles", *J. Opt. Soc. Am. A*, vol. 11, No. 9, Sep. 1994, pp. 2485-2493.

Christopher J. Raymond et al.: "Multiparameter grating metrology using optical scatterometry", *J. Vac. Sci. Technol. B*, vol. 15, No. 2, Mar./Apr. 1997, pp. 361-368.

Jörg Bischoff et al.: "New aspects of optical scatterometry applied to microtechnology", *SPIE*, vol. 3215, 1997, pp. 144-155.

Scott Bushman et al.: "Scatterometry Measurements for Process Monitoring of Polysilicon Gate Etch", SPIE, vol. 32131997, pp. 79-90, XP-000890146.

Stephen A. Coulombe et al.: "Ellipsometric-Scatterometry for sub-0.1 $\mu$m CD measurements", SPIE, vol. 3332, 1998, pp. 282-293, XP-000890148.

Jörg Bischoff et al.: "Optical scatterometry of qaurter micron patterns using neural regression", SPIE, 1998, vol. 3332, pp. 526-537, XP-000890149.

N. Benesch et al.: Application and cost analysis of scatterometry for integrated metrology, SPIE, vol. 3743, May 1, 1999, pp. 25-32, XP-000890150.

Michael R. Murnane et al.: "Developed photoresist metrology using scatterometry", SPIE, vol. 2196, Mar. 1994, pp. 47-59, XP-000890152.

Ilkka Kallioniemi et al.: "Optical scatterometry of subwavelength diffraction gratings: neural-network approach", Applied Optics, vol. 37, No. 25, Sep. 1, 1998, pp. 5830-5835, XP-000890173.

Junko Tanaka et al.: "A Sub-0.1-$\mu$m Grooved Gate MOSFET with High Immunity to Short-Channel Effects", IEDM 93, pp. 537-540.

Ken-ichiro Nakagawa et al.: "A Flash EEPROM Cell with Self-Aligned Trench Transistor & Isolation Structure", 2000 Symposium on VLSI Technology Digest of Technical Papers.

* cited by examiner

Fig. 6 ively monitoring fabrication processes of finely structured surfaces in a semiconductor fabrication and a device for carrying out the method. A comparison with existing diffraction images of tested structures is carried out in order to analyze diffraction images of the surface to be examined.

METHOD AND DEVICE FOR OPTICALLY MONITORING FABRICATION PROCESSES OF FINELY STRUCTURED SURFACES IN A SEMICONDUCTOR PRODUCTION

CROSS-REFERENCE TO RELATED APPLICATION

This application is a continuation of copending International Application No. PCT/EP99/09410, filed Dec. 2, 1999, which designated the United States.

BACKGROUND OF THE INVENTION

1. Field of the Invention

The invention relates to a method for optically monitoring fabrication processes of finely structured surfaces in a semiconductor fabrication and a device for carrying out the method. A comparison with existing diffraction images of tested structures is carried out in order to analyze diffraction images of the surface to be examined.

Specifically when fabricating semiconductors, line widths and profiles of structured layers must often be monitored during the fabrication process. Exact compliance with the specifications for the line width is of decisive importance for the functional capability of the product. In addition, further structural parameters such as trench depth or a lateral incline, for example, are of great significance. Suitable measuring devices are necessary to monitor these fabrication parameters on lithographic masks, on semiconductor wafers or on finely structured surfaces.

With the extremely small structural widths in the range of 0.25 µm which are used today, it is no longer possible to use conventional, nondestructive optical line width measuring devices due to diffraction and interference effects. So that as few monitor wafers as possible are required, cost-effective measuring methods for nondestructive and noncontaminating testing of line structures on product wafers are required in semiconductor fabrication. The measuring speed should be such that, for example, after a critical process step, each product wafer can be monitored without significantly increasing the process time.

Electron microscopes which require complex handling and have a low throughput rate are presently used for measuring line widths of fine structures (<1 µm) so that only a small proportion of the processed semiconductor wafers can be tested. Furthermore, precise measurement results for the line profiles are obtained only with what is referred to as cross section recordings, for which an already processed semiconductor wafer has to be destroyed. In addition to the regular product wafers, so-called monitor wafers are therefore also processed during the semiconductor fabrication and are subsequently used for measurement purposes. Especially with future large wafer diameters of 300 mm and above, these monitor wafers will give rise to high costs, firstly due to the material value itself, and because they significantly reduce the throughput rate of product wafers.

One approach for a solution to this problem is provided by the diffraction measurement or scattered light measuring method, referred to as scatterometry. In general, in this method the measuring region which is to be examined is illuminated and conclusions are drawn about the surface properties of the measuring region from the features of the reflected light. If there are periodic structures on the substrate, given a corresponding selection of the light wavelength, diffraction and interference effects occur. These diffraction and interference effects prevent a measurement with the usual optical devices. However, the scattered light measurement and diffraction measurement register and evaluate the diffraction and interference effects because they are characteristic for the structural variables of a measured surface. Using complex model calculations it is already possible to determine various structural variables such as line width, edge incline or line height through the use of scattered light measurement.

The reflection of coherent light at periodic structures which can be understood as amplitude or phase lattices results in diffraction effects and interference effects. If the wavelength of the light used is at least larger than half the lattice period, further maximum diffraction values of a higher order are produced in addition to the directly reflected beam of the zero-th order. The position or angle $\theta_n$ of the n-th order of diffraction depends only on the angle $\theta_i$ of incidence, on the lattice period g and on the wavelength $\lambda$:

$$\sin\theta_i + \sin\theta_n = n\frac{\lambda}{g}$$

In the case of two-dimensional lattices and complicated structures with a plurality of different periods, the diffraction problem has to be analyzed in a three-dimensional fashion. If the size of the examined structures lies in the range of the wavelength, the simple Fraunhofer diffraction equations no longer apply. Instead, the Maxwell equations for reflection and transmission in lattices must be explicitly solved, for example using what is referred to as rigorous coupled wave analysis. The nonlinearities which occur permit generally valid statements to be made only in a very limited fashion, for this reason when assessing diffraction effects on small structures it is always necessary to consider the specific individual case or to make numerical calculations.

The intensities and the phases of the orders of diffraction depend here on the properties of the incident light (angle, polarization, wavelength), on the examined lattice structure (lattice periods, line width, line height, layered structure, degree of rounding of edges, roughness) and on the material properties of the substrate (refractive index, absorption index). However, the position of the maximum diffraction values is influenced only by the angle of incidence, the lattice period and the wavelength. If these variables are constant, it is possible to draw conclusions about the other lattice parameters from the intensity evaluation of the locally fixed orders of diffraction. Because of the large number of lattice influencing variables, the lattice parameters can be determined unambiguously only if a sufficient number of measured intensity values is available for the examined measuring point.

The determination of lattice parameters by comparing the measured diffraction images with reference diffraction images which have been calculated from the circuit layout with an enormous calculation effort has, at the experimental stage, not yet been satisfactory, namely only for the case of exclusively parallel lines. Measuring devices for measuring the diffraction images according to the prior art are disclosed, for example, in Published German Patent Application No. DE 198 24 624 and U.S. Pat. No. 5,703,692. These devices are used at great cost for determining lattice parameters on strictly periodic structures when manufacturing DRAMs (Dynamic Random Access Memory) by using the following measures. In addition to the DRAM circuits, a geometrically simple test structure of parallel strips is applied to a wafer. Only its diffraction image is then measured and compared with slightly varied reference spectra of the geometrically simple test structure. The lattice parameters of the test structure result from this comparison. The parameters are used to draw conclusions about the lattice parameters of the DRAM circuits. This conclusion may not account for, for example, systematic errors of the lithographic machine or uneven plasma when generating layers or a grain of dust under the wafer.

SUMMARY OF THE INVENTION

It is accordingly an object of the invention to provide a method and a device for monitoring fabrication processes of structured surfaces in a semiconductor production which overcome the above-mentioned disadvantages of the heretofore-known methods and devices of this general type and which are cost-effective and nondestructive. The use of the method is intended to considerably reduce the equipment costs, permit a use in situ and in-line and considerably speed up the measurement and the evaluation of the measurement data.

With the foregoing and other objects in view there is provided, in accordance with the invention, a method for monitoring fabrication processes of structured surfaces in a semiconductor production, the method includes the steps of:

providing reference signatures of structured surfaces by measuring at least one distribution selected from the group consisting of a local distribution and an intensity distribution of images selected from the group consisting of diffraction images and scattered light images of a plurality of individual structures of surfaces of production prototypes having a specified quality;

measuring at least one signature of a test specimen surface to be monitored by simultaneously registering a plurality of individual structures of the test specimen surface to be monitored for providing a measured signature;

comparing the measured signature with the reference signatures for providing comparison results; and classifying parameters of the test specimen surface based on the comparison results.

Another mode of the invention includes the step of providing the plurality of individual structures such that the plurality of individual structures form a nonperiodic pattern.

Yet another mode of the invention includes the step of providing the plurality of individual structures such that the plurality of individual structures form a lattice having different periodicities along different directions.

A further mode of the invention includes the step of generating the reference signatures optically by measuring at least one of a diffraction and a scattering of an electromagnetic radiation at the structured surfaces.

Another mode of the invention includes the step of generating the at least one signature optically by measuring a diffraction and/or a scattering of an electromagnetic radiation at the plurality of individual structures of the test specimen surface to be monitored.

Yet another mode of the invention includes the step of performing the comparing step and the classifying step by using a fuzzy logic and/or a neural network having a learning capability.

Another mode of the invention includes the step of measuring individual structures of an already classified test specimen surface with a high-resolution measuring device for specifying a quality of the test specimen surface and for providing a further reference signature; and comparing a result of the step of classifying parameters of the test specimen surface to a result of the step of measuring the individual structures of the already classified test specimen surface with the high-resolution measuring device for providing a comparison result and adjusting a weighting of at least one of the fuzzy logic and the neural network as a function of the comparison result.

A further mode of the invention includes the step of generating the reference signatures by measuring the intensity distribution of the images selected from the group consisting of the diffraction images and the scattered light images while varying at least one parameter selected from the group consisting of a polarization, an angle of incidence and a wavelength of an electromagnetic radiation.

Another mode of the invention includes the step of measuring the at least one signature by measuring an intensity distribution of an image selected from the group consisting of a diffraction image and a scattered light image while varying at least one parameter selected from the group consisting of a polarization, an angle of incidence and a wavelength of an electromagnetic radiation.

Yet another mode of the invention includes the step of classifying the test specimen surface by selectively classifying the test specimen surface as a good test specimen surface and a bad test specimen surface.

A further mode of the invention includes the step of providing a classification according to graduated quality classes for classifying the test specimen surface.

Yet a further mode of the invention includes the step of providing a classification in accordance with specific production faults for classifying the test specimen surface.

Another mode of the invention includes the step of monitoring a production of periodic memory element structures or nonperiodic logic structures.

According to another mode of the invention, the step of providing the reference signatures includes producing a classification system by assigning given production prototypes having a specified quality to measurement data of the reference signatures of the given production prototypes.

According to another mode of the invention, the step of providing the reference signatures includes producing a classification system by assigning at least one of the production prototypes having the specified quality and measurement data of the reference signatures of the production prototypes to at least two classes.

According to a further mode of the invention, the step of providing the reference signatures includes providing reference signatures for different products, and the step of classifying the parameters of the test specimen surface includes identifying a product.

According to another mode of the invention, the step of providing the reference signatures includes adjusting at least one of the production prototypes in different ways, and the step of classifying the parameters of the test specimen surface includes classifying a misadjustment of a test specimen.

Another mode of the invention includes the step of providing the structured surfaces as microstructured surfaces, in other words as finely structured surfaces.

With the objects of the invention in view there is also provided, a device for monitoring fabrication processes of structured surfaces in a semiconductor production, including:

a reference signature apparatus for providing reference signatures of structured surfaces, the reference signature apparatus being configured for performing a measurement of reference signatures by measuring at least one distribution selected from the group consisting of a local distribution and an intensity distribution of images selected from the group consisting of diffraction images and scattered light images of a plurality of individual structures of a surface of production prototypes having a specified quality;

a measuring apparatus operatively connected to the reference signature apparatus, the measuring apparatus measuring at least one signature associated with a test specimen surface to be monitored by simultaneously registering a plurality of individual structures of the test specimen surface to be monitored for providing a measured signature;

a comparison module operatively connected to the measuring apparatus, the comparison module comparing the measured signature with the reference signatures and providing comparison results; and a classification module operatively connected to the comparison module, the classification module classifying parameters of the test specimen surface through the use of the comparison results.

According to another feature of the invention, the reference signature apparatus, the measuring apparatus, the comparison module, and the classification module are integrated in a semiconductor fabrication line for providing at least one of an in situ production monitoring and an in-line production monitoring.

According to another feature of the invention, the measuring apparatus includes an electromagnetic radiation source for providing a coherent electromagnetic radiation, a rotation apparatus for rotating a polarization of the coherent electromagnetic radiation, the rotation apparatus rotating the polarization in one of an infinitely adjustable manner and in small increments, and at least one electromagnetic radiation detector; and the measuring apparatus is configured such that the coherent electromagnetic radiation hits a structured test specimen surface at a fixed angle of incidence, and such that one of a local distribution and an intensity distribution of a diffraction image generated by reflecting the coherent electromagnetic radiation at the structured test specimen surface is measured as a function of the polarization by using the at least one electromagnetic radiation detector.

According to yet another feature of the invention, the measuring apparatus includes an electromagnetic radiation source for providing an electromagnetic radiation with a given wavelength, the wavelength is selected such that dimensions of the individual structures of the test specimen surface are of a same order of magnitude as the given wavelength.

According to a further feature of the invention, the measuring apparatus includes an electromagnetic radiation source for providing an electromagnetic radiation with one of a plurality of wavelengths and a plurality of wave length ranges; and the measuring apparatus carries out a measurement one at a time as a function of the one of the plurality of wavelengths and the plurality of wave length ranges.

According to another feature of the invention, the measuring apparatus includes an electromagnetic radiation source for providing an electromagnetic radiation with one of a plurality of wavelengths and a plurality of wave length ranges; and the measuring apparatus carries out a measurement simultaneously with the one of the plurality of wavelengths and the plurality of wave length ranges.

According to yet another feature of the invention, the measuring apparatus includes a spectral lamp for providing coherent light and filters for extracting various wavelength ranges from the coherent light.

According to another feature of the invention, the measuring apparatus includes an electromagnetic radiation source for providing an electromagnetic radiation and a rotation apparatus for rotating a polarization of the electromagnetic radiation; the rotation apparatus rotates the polarization in one of an infinitely adjustable manner and in small increments, and the rotation apparatus is selected from the group consisting of a $\lambda/2$ plate, two $\lambda/4$ plates, an electro-optical element, and a mechanical rotating apparatus for mechanically rotating the electromagnetic radiation source.

According to yet another feature of the invention, a movable mounting table is provided for holding a test specimen when measuring at least one distribution selected from the group consisting of a local distribution and an intensity distribution of diffraction images in various regions of the test specimen.

According to a further feature of the invention, the measuring apparatus is moved with respect to a test specimen when measuring at least one distribution selected from the group consisting of a local distribution and an intensity distribution of diffraction images in various regions of the test specimen According to another feature of the invention, the measuring apparatus examines an electromagnetic radiation reflected by the test specimen surface to be monitored.

According to an additional feature of the invention, the classification module includes a diffraction simulator for determining absolute profile parameters from the measured signatures.

Other features which are considered as characteristic for the invention are set forth in the appended claims.

According to the invention, the classification for monitoring or checking a semiconductor fabrication is carried out during production as follows: in a pre-run, a sufficiently large number of structures to be examined (prototypes with typical production deviations) are measured, for example, with the measuring device proposed below and diffraction images and/or scattered light images (signatures) are thus recorded. In this way a number of reference signatures is obtained. Furthermore, the test specimens are examined with a measuring device in accordance with the prior art which supplies absolute measured values (for example an electron microscope). A database is thus obtained which contains the classification of the reference signatures and which permits faulty parts to be assigned to the diffraction/scattered light images of the surfaces of test specimens from the production (measuring signatures). By using this database it is thus then possible to train a classifying system, for example a neural network with learning capability and further to carry out a classification into "good" and "bad." The measurements with the electron microscope can be eliminated. Finer classifications into a plurality of classes (for example direction of the deviations) can also be carried out. Furthermore, the effects of deviations of various parameters can be separated and also integrated into the classification model (the database simply has to be large enough for that, for example several hundred test specimens). With this method it is possible to examine test specimens which are not accessible to modeling due to their complexity. This is especially the case with typical product structures in semiconductor fabrication (for example in the case of a DRAM). With a modeling method according to the prior art, it was necessary under certain circumstances to use special test structures which permitted parameter variations to be simulated. This meant considerable fabrication cost, and could rule out the use of the measuring method.

For each structure type and respectively for each product of a semiconductor factory it is necessary to carry out this training of the parameters which are characteristic for the product type by measuring prototypes. It is not possible to transfer them from one product to another. It is then possible to detect parameter deviations within a product type. The same applies also to the modeling approach according to the prior art.

A further interesting application (of scattered light measurement/diffraction measurement) is product detection. Of course, the measuring signatures as a rule differ considerably and unambiguously from one product to another. As a result, the detection of products (of different semiconductor structures) becomes possible in a very cost-effective way and it is possible to dispense with, or replace, costly image detection or detection of lettering. A further problem in semiconductor factories is associated with this. In the case of misdirected wafers, the fabrication step (for example a small etching step), and the state in which the wafer is now in, can be determined only with a relatively high degree of effort. Through the use of a scattered light/diffraction measurement, this allocation could be made in fractions of a second if the diffraction signatures after each fabrication step has been recorded and stored once in advance. The assignment is then made through the use of a comparison (for example with a table and/or a neural network).

This product detection/assignment to a process step can be applied not only to periodic structures when using a diffraction analysis. Characteristic intensity profiles can also occur in general, nonperiodic (logic) structures and thus permit a classification. This extension to nonperiodic structures is also possible for the classification of parameter deviations.

According to the invention it is proposed to compare the intensity distributions of diffraction images with the intensity distributions which have previously been recorded with specified, optimum lattice structures and/or production prototypes and to decide through the use of a suitable spacing dimension whether the specifically examined structure complies with the required specification.

For this classification (for example "structure satisfactory/process faulty") there is no need for complex model formation or for absolute lattice variables to be determined. Instead, the intensity curves of test specimens which fulfill the specifications (prototypes) are stored using a system with learning capability and a comparison is made with the current measured curve. Absolute lattice variables are obtained by measuring reference prototypes using independent methods (for example an electron microscope) which are assigned to the reference signatures. A tedious calculation pre-run is eliminated, in particular a coarse classification into good or bad can be carried out with even a small number of reference signatures.

The method described is suitable specifically for the continuous monitoring of regular structures, for example memory elements which have symmetrical lattice structures for the most part. Whereas the previous methods with numerical simulations were mainly suitable for simple test structures, the scheme proposed here can also be applied to complex product structures. When the fabrication line is started up, sufficient measurement data are obtained from scanning electron microscope investigations for training a classifying system with a learning capability (for example a neural network or a fuzzy logic).

In order to assess the structured test specimen surface, the intensity profiles are compared with curve profiles of specified test specimens (prototypes). A system with a learning capability, for example a neural network, is used to classify the respective test specimen surface (for example a classification in "good" and "bad"). For this purpose, the neural network has been trained with a sufficient number of exemplary structures (prototypes). After a faulty structure has been detected, it can be examined precisely with the costly methods of the prior art. The great advantage of this method lies in its simplicity. There is no need for a highly qualified specialist whose function is to model the test specimen surfaces as precisely as possible and to predict the scattered light and diffraction effects in order to obtain an absolute measured value for one or more lattice parameters. Instead, the classification into good/bad, which is important for fabrication, or at least a warning can be obtained very quickly and simply. The method can thus also be used efficiently for lattice structures which have a plurality of periodicities in various spatial directions (2D lattices) and which are difficult to model as a result of rounded edges, roughnesses or unknown material properties. However, as with similar measuring methods (or for example in the case of ellipsometry) it is, of course, also possible to determine absolute measurement results with the measuring device presented below through the use of simulation and regression of the model parameters.

As a further application of the present invention it is possible to detect a faulty adjustment of the test specimen. An unintentional tilting or rotation of the test specimen during measurement brings about a change in the angle of incidence of the light and leads, under certain circumstances, to significant deviations in the intensity curves. The training data for a classifying, neural network which are obtained from real trials also contain such random tilting, with the result that the system automatically takes into account such effects and the structural expenditure to avoid and detect such tilting can be kept relatively small.

Furthermore, the intensities of the higher order diffraction maxima can also be used for a correct alignment of the wafer. In general, the diffraction orders to the left and right of the direct reflection have different intensities if the lattice vector which describes the periodicity of the structures does not lie in the plane of incidence of the light beam or the test specimen is rotated. In this way, a very simple and sensitive way of detecting a rotation of the wafer is obtained, which acts on the intensity profiles to be measured and can thus falsify the measurement result for the structural variables.

It must be noted that a particularly large advantage of the method according to the invention is that, it does not require any model formation which permits a reverse calculation of the measured intensity profile in a test specimen in order to arrive at absolute structural variables of this test specimen. There are generally no analytical approaches available for this reverse calculation. Instead, as many conceivable parameter combinations as possible must be simulated in advance and the resulting intensity curves must be entered, for example, into a table. The reverse calculation is then composed essentially of a comparison of the table curves with the currently measured curve. In the case of complex lattice structures, these advance simulations can become very extensive/costly and last days or weeks.

However, for process monitoring the important factor is essentially to monitor the specifications such that a conclusion about "satisfactory" or "not satisfactory" is possible (if appropriate also information relating to the direction of a deviation). The invention proposes that only such a classification should be carried out. For this purpose, only a signature which is as unambiguous as possible for the parameters to be monitored is measured. It is necessary to ensure here that specific signatures unmistakably indicate specific surface structures. These signatures may be, for example:

the intensity of the orders of diffraction given variable polarization of the measuring beam, the intensities of the orders of diffraction (or only of the direct reflex) when the angle of incidence of the measuring beam changes, measured values psi/delta of an ellipsometer (if appropriate a parameter such as polarization, wavelength, angle of incidence is changed in order to obtain more information on the structure and thus a signature which is as unambiguous as possible), measurements with spectroscopy, reflectometry, thermowave analysis, X-ray spectroscopy: the measured values which are obtained in this way depend on the structure parameters (line width/layer thickness) in a complex way. Absolute structural variables can thus be obtained only with difficulty, but a simple distinction between different structures is possible.

Irrespective of the actual measuring principle, the basis of the method is to generate measuring signatures which can be assigned unambiguously to different lattice parameters.

A measuring setup for generating polarization-dependent signatures is described below. A light source supplies coherent, linearly polarized light of one wavelength. Alternatively, unpolarized light may be polarized linearly through the use of appropriate polarizers. In addition, a plurality of beams of various wavelengths may be combined to form one beam in order to obtain a larger number of diffraction maxima. The coherent light can also originate from a spectral light source (for example a xenon lamp), various wavelength ranges being extracted using a filter. The evaluation, described below, of the light intensity reflected by the surface can thus additionally be carried out as a function of the wavelength. The measurement precision and the sensitivity of the method can be increased using the additional parameter.

Through the use of a suitable optical element (for example a $\lambda/2$ plate), the polarization angle during the measurement is changed in an infinitely adjustable way or in small increments (by motor). Alternatively, an electro-optical element can also be used for a polarization rotation or the linearly polarized light source (the laser) is itself rotated. The beams are guided using lenses, mirrors and prisms, their precise configuration not changing the underlying measuring principle in any way. However, the effects of the optical elements on the polarization angle of the incident light beam must be taken into account. The mirrors, prisms or wafers can be provided in any desired sequence between the light source, $\lambda/2$ plate and the test specimen to be examined. The decisive factor is that a linearly polarized light beam is incident on the test specimen surface whose polarization angle is varied between 0° and 180°. Alternatively, a different angular range between 0° and 360° may also be selected. However, angles above 180° do not supply any basically new information but rather constitute a repetition of the measurement between 0° and 180°. The measuring method can also be carried out with elliptically polarized light. As in the linear case, the azimuth angle (polarization angle) which determines the main axis of the elliptically polarized light is predefined using a $\lambda/2$ plate. The respectively required elliptical polarization is obtained from linearly polarized light, again using a suitable optical element (for example a $\lambda/4$ plate). In order to take into account the noise of the light source, the intensity of a reference beam extracted with a beam splitter (for example prism or beam plate) is measured using, for example, a photodiode. An angle of incidence which is suitable for the respective test specimen is implemented using a beam deflection which is adjustable but fixed during the measurement (see above with respect to beam guidance). This constant angle of incidence of the light beam on the test specimen constitutes an important difference from previously proposed similar measuring devices and simplifies the measuring setup considerably.

Given a diameter of approximately 0.5 mm, the light beam generally strikes several thousand individual structures so that the measurement result constitutes an average value for the respective lattice parameters. If desired, the light beam can be widened using an optic system in order to increase the number of individual structures which are considered simultaneously. Here, nonperiodic structures may also be registered. In the case of largely nonperiodic structures, conclusive information about the roughness or the average surface condition of the test specimen is obtained with the measuring method. The light beam can also be focused in order to cover only a small number of individual structures if the region of periodic structures is small or because the properties of specifically these individual structures are of interest. Using a movable mounting table it is possible to approach various measuring points on a relatively large test specimen surface (mapping). As an alternative it is also possible to move and position the measuring unit.

The lattice variables determine the light distribution starting from the reflection point. In the simplest case, only the intensity of the directly reflected beam is measured as a function of the polarization angle using a photodiode. As a variation, the reflected beam can in turn be examined through the use of a variable polarizer (analyzer) for specific polarization angles. As in the case of an incident light beam, mirrors and prisms can be used for guiding and deflecting the beam without influencing the measuring principle. If higher orders of diffraction occur, they can also be measured with adjustable photodiodes. One or more curve profiles are obtained per measuring point and are used for classifying a lattice parameter or determining it in absolute terms. The lattice parameters here are lattice periods, line widths, trench depths, layer thicknesses (also transparent multilayer systems), sidewall gradients (inclines), degrees of rounding of edges and surface roughnesses and material properties (for example refractive index). The test specimen surface can be covered by metals (for example aluminum), semiconductors (for example polysilicon) or nonmetals (for example coating agents). The field of application of the measuring principle or the possible size of the fine surface structures depends on the wavelength of the electromagnetic radiation used, the sizes of the structures should correspond in its order of magnitude to the wavelength.

Furthermore, measurement systems with local resolution, for example a CCD (charge-coupled device) camera (possibly with a screen positioned intermediately) can be used for registering the intensity.

Due to its simple configuration with fixed components and the evaluation of a very small scattered light angle, the proposed structure is suitable as an integratable in situ or in-line device, in contrast to the previously proposed line width measuring configurations.

Whereas, in the known scattered light measurement with constant polarization of the light source, the angle of incidence or the measured angle of emergence can be varied with costly measuring configurations, it is proposed here to continuously rotate the linear polarization in order to considerably simplify the measuring configuration and speed up the measuring process.

The measurement result obtained includes intensity profiles of the orders of diffraction (in the simplest case only the 0-th order of diffraction) as a function of the polarization angle between 0° and 180°. For this purpose, the lattice vector which gives the direction of periodicity must not lie in the plane of incidence of the light beam so that conical diffraction occurs.

However, the application of the method according to the invention is not restricted to varying the polarization of the light beam used for the measurement. It is equally suitable to vary the angle of incidence (vertical angle and/or azimuthal angle) of the light beam on the test sample in order to generate different diffraction images. An apparatus for varying the angle of incidence may, for example, be as follows.

The measuring configuration such as in Published German Patent Application No. DE 198 24 624 A1 can be used. However, the beam splitter is replaced by a mirror which is rotated in an electrically controlled fashion. The mirror which rotates in an electrically controlled fashion (referred to as galvanometer scanner) is used in conjunction with a fixed, nonplanar mirror surface in order to vary the angle of incidence of the measuring beam for a 2θ diffraction analysis of a fixed measuring point. Such a configuration permits large angular settings to be established within milliseconds with a precision of several μrad. The angle of incidence can be varied within several tenths of a second. Moreover, what is required to generate different angles of incidence is only one robust movable component (galvanometer scanner), thus reducing the susceptibility to faults. The costs of the components used and the spatial requirement necessary for the measuring setup are comparatively low. Because different angles of incidence are generated sequentially, there is precisely one incident measuring beam at each moment in time. There is thus no superposition of orders of diffraction.

Furthermore, it is proposed to use the intensities of the first order of diffraction for testing the precise alignment of the test specimen wafer.

The two maximum values of diffraction of the first order have the same intensity with conical diffraction only at a specific rotational angle of the wafer on the test stand. This provides a simple way of precisely adjusting the angle of rotation which influences the intensity profiles. The intensity profiles can conventionally be used with a model for determining absolute lattice variables through the use of parameter regression.

Other features which are considered as characteristic for the invention are set forth in the appended claims.

Although the invention is illustrated and described herein as embodied in a method and device for optically monitoring fabrication processes of finely structured surfaces in a semiconductor fabrication, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
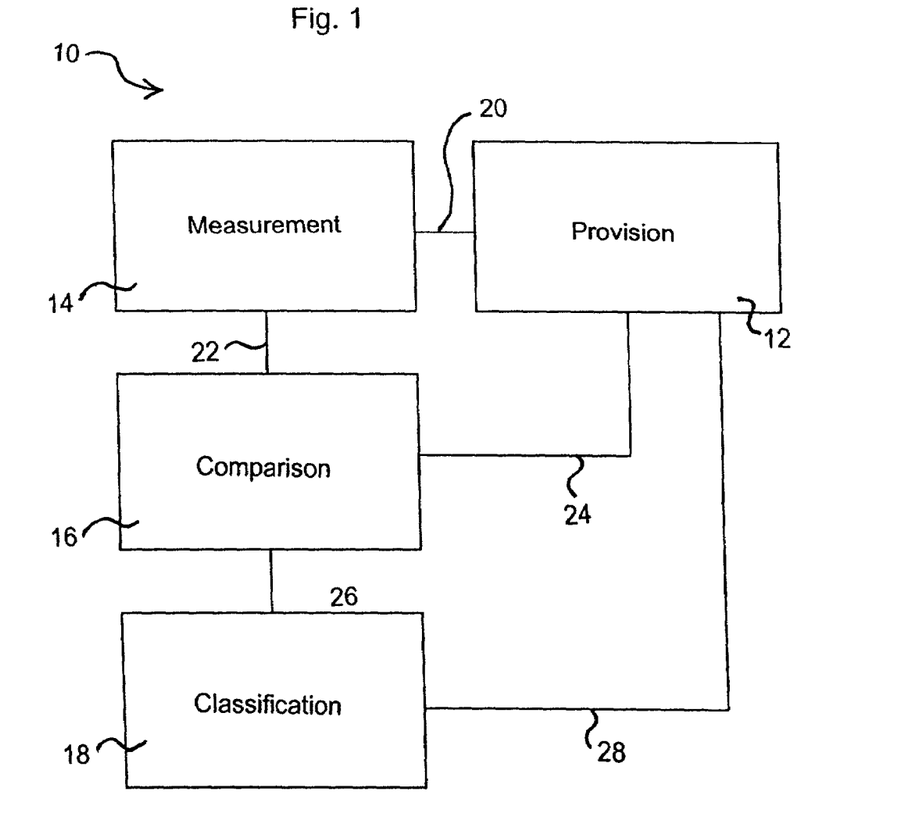
FIG. 1 is a block diagram of a device according to the invention.

Referring now to the figures of the drawings in detail and first, particularly, to FIG. 1 thereof, there is shown a device 10 for monitoring fabrication processes of finely structured surfaces in semiconductor fabrication according to the present invention. The device 10 is composed of an apparatus 12 for providing reference signatures of finely structured (microstructured) surfaces, an apparatus 14 for measuring at least one signature of the test specimen surface to be monitored, a module 16 for comparing the measured signature with the reference signatures and a module 18 for classifying parameters of the test specimen surface by reference to the comparison results. The device 12 for providing reference signatures is equipped for carrying out a measurement of the reference signatures by measuring the local distribution and/or intensity distribution of diffraction images on production prototypes of specified quality.

The device 10 is integrated into a semiconductor fabrication line and permits in situ and in-line production monitoring. For this purpose, production prototypes are measured with the measuring apparatus 14 and a signature of the test specimen surface is obtained from each production prototype. The production prototypes are subsequently measured in quantitatively absolute terms by analysis using different method parameters and specified qualitatively. This qualitative specification includes a predetermined classification range with very good, good, still usable, inadequate and very poor classes. The reference signatures are transmitted via the link 20 to the apparatus 12 for providing reference signatures. The signatures, the classifications and the parameters are stored assigned to one another in the apparatus 12 for providing reference signatures. The device 10 is then prepared for monitoring fabrication processes of finely structured surfaces in semiconductor fabrication. The monitoring of fabrication processes takes place in that test specimens which are to be monitored are measured in the measuring apparatus 14 and in each case a signature of the test specimen surface to be monitored is measured. The signature of a test specimen is transmitted via connection 22 and reference signatures are transmitted via connection 24 to the module 16 for comparing the measuring signature with the reference signatures and compared with one another in the comparison module 16. Results of this comparison of the signatures are passed on to the module 18 for classifying parameters of the test specimen surface via connection 26. The classification module 18 receives classification data and parameters of the reference test specimens from the apparatus 12 for providing reference signatures via connection 28, the reference test specimens being assigned to those reference signatures which comparison has shown to be relevant. The classification module 18 carries out a classification of the currently measured test specimen surface using this data and determines the absolute profile parameters of the specimen surface using a diffraction simulation.

Figure 2:
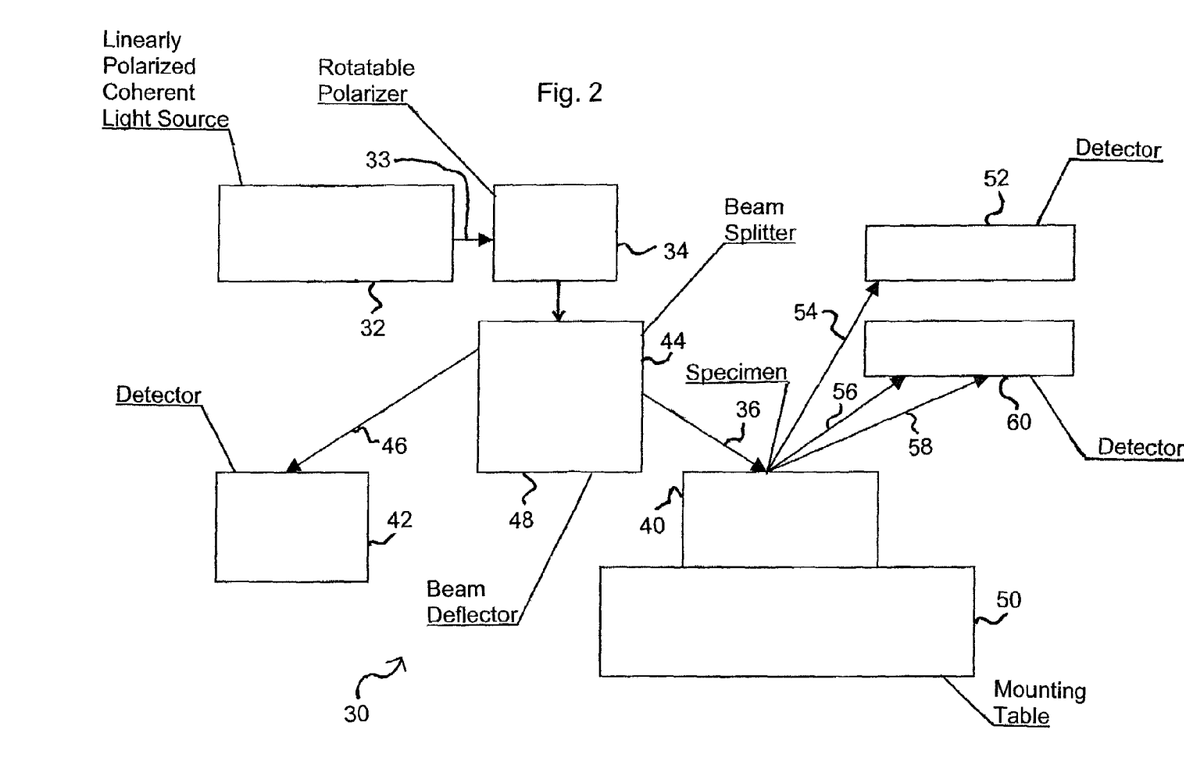
FIG. 2 is a block diagram illustrating the structure of an apparatus for measuring signatures as part of the implementation of the device of FIG. 1 in accordance with an embodiment in which the polarization of the light used for the measurement is varied.

FIG. 2 shows the setup of an apparatus for measuring signatures 14 within the device 10 of FIG. 1 in an embodiment in which the polarization of the light used for the measurement is varied. The apparatus for measuring polarization-dependent signatures 30 has a light source 32 which supplies coherent, linearly polarized light of one wavelength with the beam 33. Alternatively, nonpolarized light can be linearly polarized through the use of appropriate polarizers. The polarization angle is varied in an infinitely adjustable fashion or in small increments (by a motor) during the measurement through the use of a polarizer 34 (for example a λ/2 plate). Alternatively, an electro-optical element can be used for polarization rotation or the linearly polarized light source (the laser) is rotated itself. A linearly or elliptically polarized light beam 36 is incident on the surface of the test specimen 40 whose polarization angle (azimuth) is preferably varied between 0° and 180°. Alternatively, a different angular range between 0° and 360° can also be selected or the measurement can be repeated with other angles in order to increase the measuring accuracy. In order to make allowance for the noise of the light source, the detector 42, for example a photodiode, is used to measure the intensity of a reference beam 46 which is extracted with a beam splitter 44 (for example prism or beam plate). An angle of incidence which is suitable for the respective test specimen 40 is selected using an adjustable beam deflector 48 which is however fixed during the measurement. This constant angle of incidence of the light beam 36 on the test specimen constitutes a simplification in comparison with devices measuring which measure a signature as a function of the angle of incidence. Various measuring points on a relatively large test specimen surface can be approached using a movable mounting table 50.

The lattice variables determine the light distribution emerging from the reflection point. In the simplest case, only the intensity of the directly reflected beam 54 (mirror reflex) is measured with a detector 52, for example a photodiode, as a function of the polarization angle. If higher orders of diffraction occur, secondary reflexes 56, 58, they can also be measured with adjustable detectors 60, for example photodiodes or a CCD camera.

The measurement data is evaluated and the system controlled using a computer system connected to the individual parts of the device, which computer system also includes the classification module, preferably the system with learning capability, composed of a neural network. If a physical model for the simulation of the diffraction effects is used according to the prior art, the intensity curves measured with the configuration can also be used for calculating absolute test specimen data, in particular profile parameters.

The apparatus for measuring a polarization-dependent signature 30 is preferably composed of a coherent electromagnetic radiation source 32, an apparatus for rotating the polarization 34 of the electromagnetic radiation in an infinitely adjustable fashion or in small increments, and at least one electromagnetic radiation detector 52, 60, coherent electromagnetic radiation being incident on a finely structured test specimen surface at a fixed angle of incidence, and the local distribution and/or intensity distribution of the diffraction image generated on the surface by the reflection of the radiation being measured with at least one radiation detector 52, 60 as a function of the polarization of the illuminating radiation 36. The illuminating electromagnetic radiation is polarized either linearly or elliptically. Its wavelength is in the range of the structure sizes of the structures on the finely structured surface and includes a plurality of wavelengths or wavelength ranges. The measurement is carried out either as a function of the wavelengths or wavelength ranges in succession or with all the wavelengths or wavelength ranges simultaneously.

The coherent light advantageously originates from a spectral lamp and the various wavelength ranges are extracted with a filter. The apparatus for rotating the polarization of the electromagnetic radiation in an infinitely adjustable fashion or in small increments is preferably composed of a λ/2 plate or of two λ/4 plates or of an electro-optical element or of an apparatus for mechanically rotating the light source itself.

The test specimen with the finely structured surface is preferably secured to a movable mounting table or the entire measuring apparatus is moved with respect to the test specimen and measurements of local distributions and/or intensity distributions of diffraction images are carried out on various regions of the test specimen surface.

The electromagnetic radiation reflected from the finely structured surface is advantageously examined as a function of its polarization.

Figure 3:
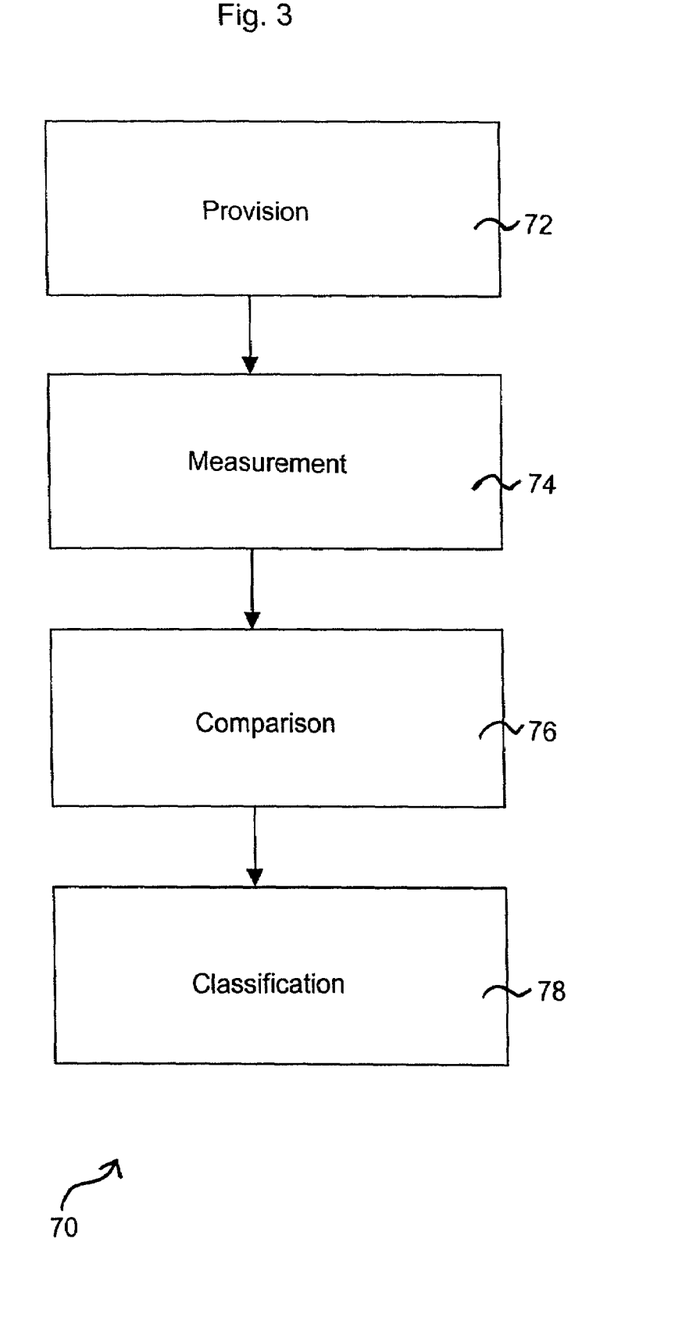
FIG. 3 is a flowchart of the method according to the invention.

FIG. 3 shows a flowchart 70 of the method according to the invention for monitoring fabrication processes of finely structured surfaces in semiconductor fabrication. The method is composed of the steps of providing reference signatures 72 of finely structured surfaces; measuring at least one signature 74 of a test specimen surface which is to be monitored; comparing 78 the measuring signature with the reference signatures; and classifying 78 parameters of the test specimen surface through the use of comparison results, the provision of the reference signatures 72 including the step of measuring the local distribution and/or intensity distribution of diffraction images on production prototypes having a specified quality.

The signatures are preferably generated in an optical fashion by measuring diffraction and/or scattering of electromagnetic radiation on the finely structured surfaces. The comparison of the signature of the test specimen surface with the reference signatures and its classification are carried out using a neural network with learning capability and/or a fuzzy logic. The signatures are generated by measuring the intensity distribution of diffraction images and/or scattered light images while varying at least one member of the group composed of polarization, angle of incidence and wavelength of the electromagnetic radiation. The classification of the test specimen surface includes classification into good or bad and/or classification into finely graduated quality classes and/or assignment to specific production faults.

The method is advantageously used for monitoring the production of periodic memory element structures and/or nonperiodic logic structures. The provision of reference signatures includes generating a classification system with an assignment of a classification of the production prototypes of specified quality to the measurement data of the reference signatures on the same production prototypes.

In one advantageous embodiment, the provision of reference signatures includes different products and the classification of parameters of the test specimen surface includes the identification of the product of the test specimen.

The provision of reference signatures preferably includes different adjustments of the same production prototypes and the classification of parameters of the test specimen surface includes a maladjustment of the test specimen.

Figure 4:
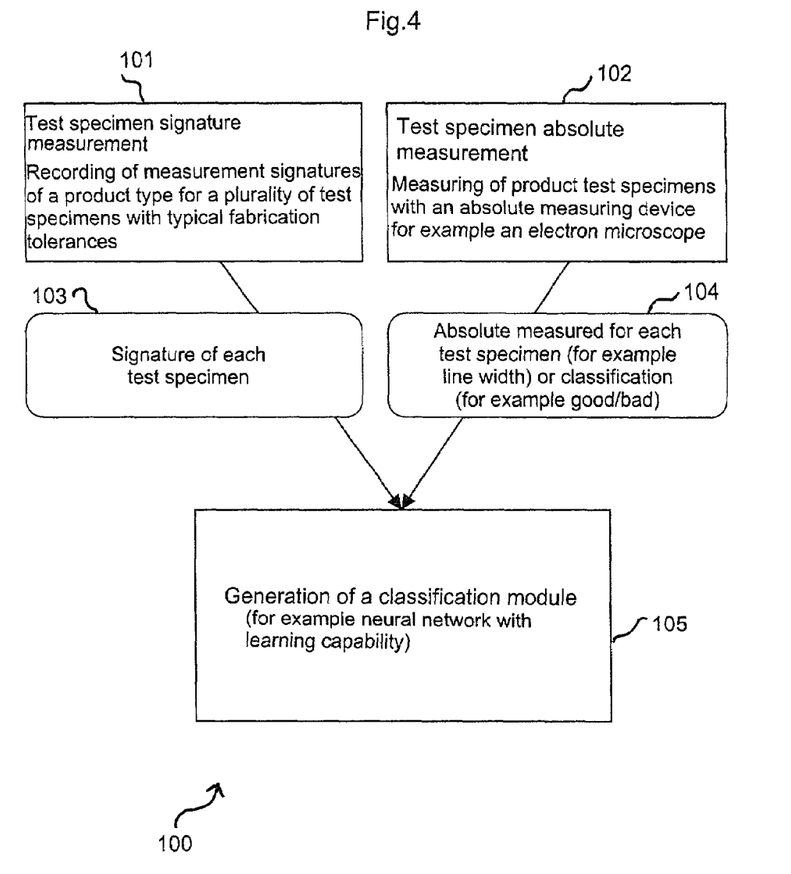
FIGS. 4 and 5 are flowcharts for illustrating the method according to the invention in accordance with a further embodiment.
Figure 5:
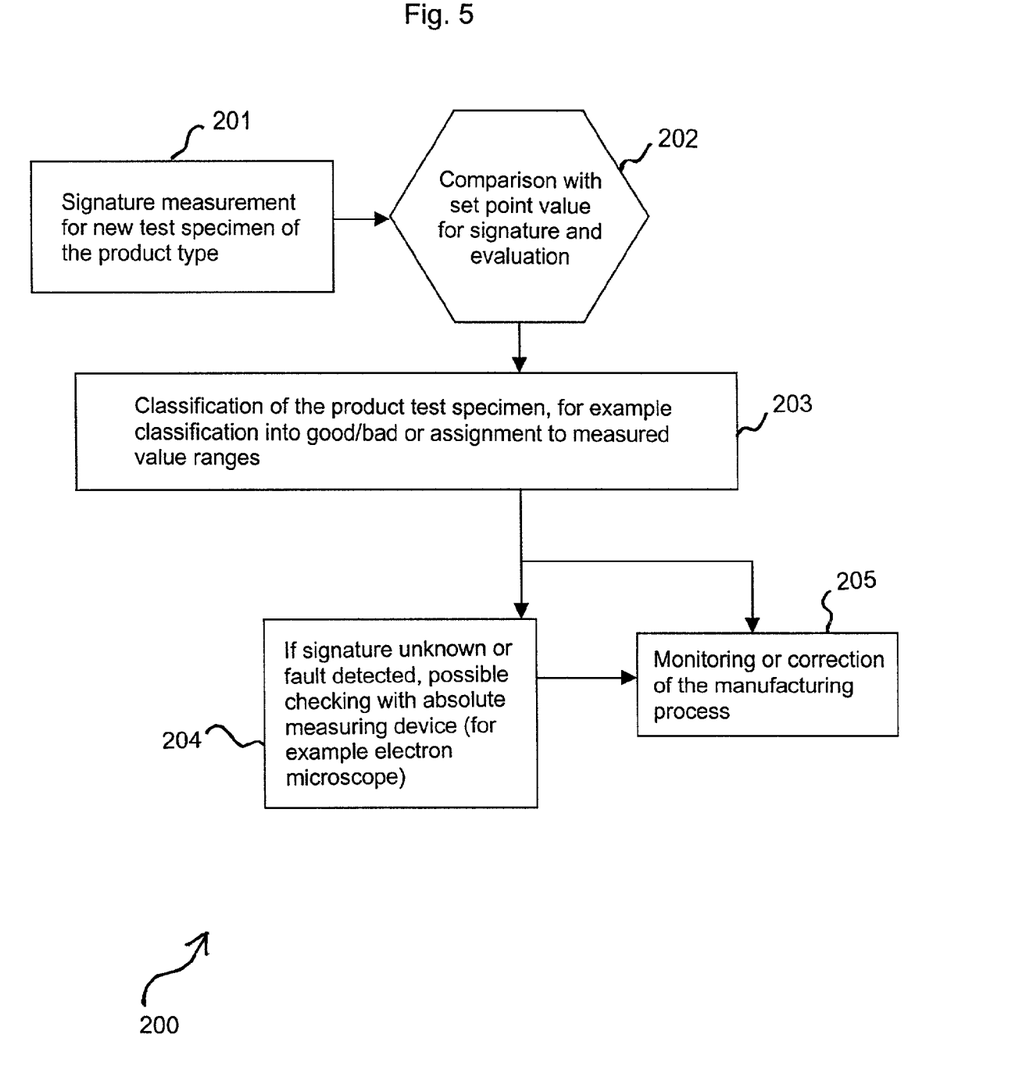

FIGS. 4 and 5 illustrate the method according to the invention through the use of a flowchart. The method steps are divided into method sections of a pre-run 100 (FIG. 4) and a production process section 200 (FIG. 5). The method section pre-run 100 contains the method step of providing reference signatures and describes this step in substeps. In the pre-run 100 (training of the system), a sufficiently large number of the structures to be examined (prototypes with typical production deviations) is measured by measuring the local distribution and/or intensity distribution of diffraction images on production prototypes (step 101) of a specified quality. In this way, a number of reference signatures is obtained (step 103). Moreover, the test specimens are examined (step 102) with a measuring device according to the prior art (for example an electron microscope) which supplies absolute measured values, as illustrated in step 104. The reference signatures can thus be assigned to the absolute measured values of these test specimens (production prototypes). In this way, a database, which permits faulty parts to be assigned to the diffraction/scattered light images of the surfaces of test specimens from production (measuring signatures), is obtained. By using this database, it is then possible, for example, to train a neural network and potentially even to perform a classification into "good" and "bad" as shown in step 105. In this way, reference signatures of finely structured surfaces are provided for the production process section 200.

In the production process section 200, at least one signature of a test specimen surface which is to be monitored is firstly measured in step 201 by measuring the diffraction and/or scattering of electromagnetic radiation on the finely structured surfaces. The signatures are generated by measuring the intensity distribution of diffraction images and/or scattered light images while varying at least one element of the group including polarization, angle of incidence and the wavelength of the electromagnetic radiation. Subsequently, the measuring signature is compared with the reference signatures in step 202. The similarity of the signature and reference signatures is evaluated here and in a normal case at least one reference signature is identified as similar. Then, in step 203, parameters of the test specimen surface are classified through the use of the comparison results. According to the invention, it is concluded that the test specimen surface has properties similar to the identified reference test specimen and can be classified in the same class as the latter. If no reference signature is identified as similar, it is concluded according to the invention that the test specimen is faulty. Through the use of a suitable spacing dimension it is decided whether the specifically examined structure contains the required specifications. This classification of the test specimen surface is part of a classification into good or bad and/or a classification into finely graduated quality classes and/or an assignment to specific production faults. The comparison of the signature of the test specimen surface with the reference signatures and its classification are carried out using a neural network with a learning capability and/or a fuzzy logic. In the case of faults, a precise fault examination with absolute measuring devices according to the prior art can be carried out in step 204. This fault analysis can lead, in step 205, to a correction of the manufacturing process.

Figure 6:
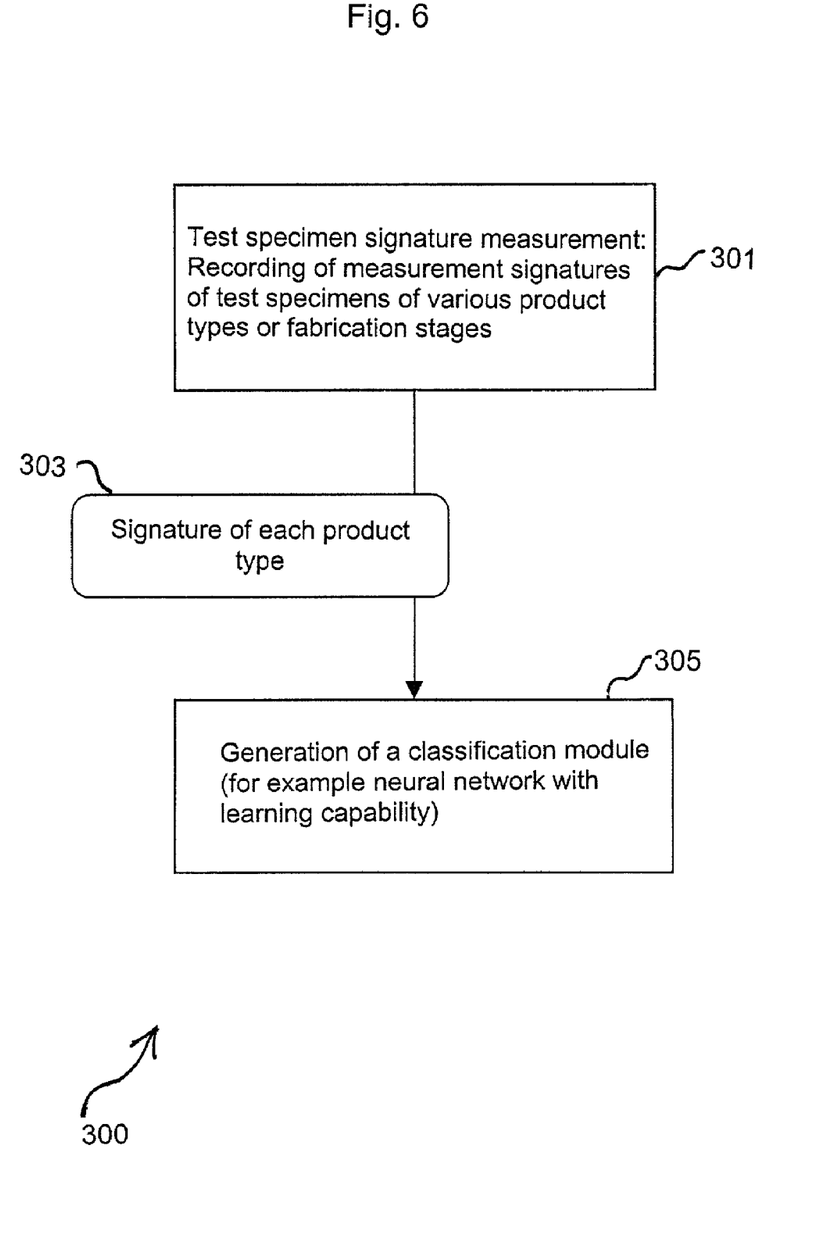
FIGS. 6 and 7 are flowcharts for illustrating the use of the method according to the invention for a product detection.
Figure 7:
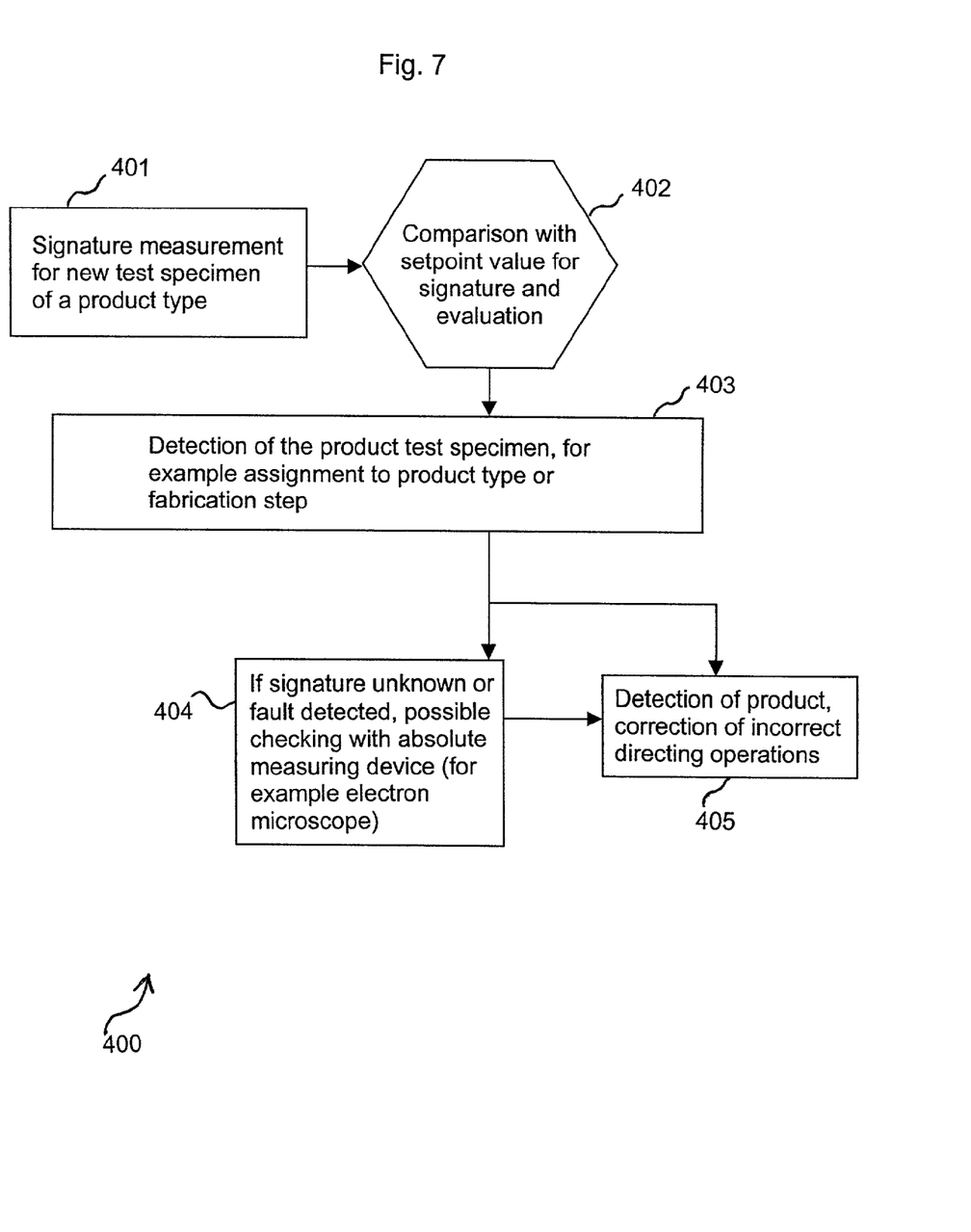

In FIGS. 6 and 7, the use of the method according to the invention for product detection is illustrated through the use of a flowchart. The method steps are divided up into the method section of a pre-run 300 (FIG. 6) and a production process section 400 (FIG. 7). The method section pre-run 300 contains the method step of providing reference signatures and describes it in substeps. In the pre-run 300 (training of the system), a sufficiently large number of the structures to be examined (various product types in various fabrication stages and/or with various production faults) are measured by measuring the local distribution and/or intensity distribution of diffraction images on production prototypes of specified quality (step 301). In this way, a number of reference signatures is obtained in step 303. Through the use of this database it is then possible to train, in step 305, a neural network and in potentially even perform a product detection. In this way, reference signatures of finely structured surfaces are provided for the production process section 400 illustrated in FIG. 7.

In the production process section 400, at least one signature of a test specimen surface which is to be monitored is firstly measured in step 401 by measuring the diffraction and/or scattering of electromagnetic radiation on the finely structured surfaces. Subsequently, the measuring signature is compared with the reference signatures in 402. Here, the similarity of the signature to reference signatures is evaluated and in a normal case at least one reference signature is identified as similar. Then, in step 403, parameters of the test specimen surface are classified through the use of the comparison results. According to the invention, it is concluded that the test specimen surface has properties similar to the identified reference test specimen and the test specimen is identified as the same product as this reference test specimen. In this context, different manufacturing stages are understood to result in different products during the manufacture of one type of product. If no reference signature is identified as similar, it is concluded according to the invention that the test specimen is faulty. In the case of faults, a precise fault examination with absolute measuring devices according to the prior art can be carried out in step 404. This fault analysis can lead to a correction of the manufacturing process (step 405).

With the above described method it is possible to detect product batches and correct a misrouting or incorrect operation. In addition, various manufacturing stages up to the finishing of the semiconductor product can be distinguished.

We claim:

1. A method for monitoring fabrication processes of structured surfaces in a semiconductor production, the method which comprises:

generating reference signatures of structured surfaces by measuring an intensity distribution of images varying at least a wavelength and a polarization of an electromagnetic radiation, the polarization of the electromagnetic radiation being varied by a rotation apparatus rotating an electromagnetic radiation source, the images being selected from the group consisting of diffraction images and scattered light images of a plurality of individual structures of surfaces of production prototypes having a specified quality;

providing at least one of a neural network and a fuzzy logic having a learning capability by adjusting a weighting of the at lease one of the neural network and the fuzzy logic as a function of the reference signatures;

measuring at least one signature of a test specimen surface to be monitored by simultaneously registering a plurality of individual structures of the test specimen surface to be monitored by using an intensity distribution of images varying at least a wavelength and a polarization of an electromaqnetic radiation, the polarization of the electromagnetic radiation being varied by a rotation apparatus rotating an electromagnetic radiation source, the images being selected from the group consisting of diffraction images and scattered light images for providing a measured signature;

performing measurements for both the reference signatures and the at least one signature of the test specimen surface to be monitored one at a time;

comparing the measured signature with the reference signatures for providing comparison results by using at least one of the fuzzy logic and the neural network to evaluate similarity between the reference signatures and the measured signature; and if a similarity between the reference signatures and measured signature has been found in the comparison step, then performing the step of:

classifying parameters of the test specimen surface based on the comparison results;

or otherwise performing the steps of:

measuring individual structures of the test specimen surface with a high resolution measuring device for providing absolute quantities of the individual structures on the surface with high resolution and for providing a further reference signature; and adjusting the weighting of at least one of the fuzzy logic and the neural network as a function of the further reference signature;

classifying parameters of the test specimen surface based on the measurement of the individual structures.

2. The method according to claim 1, which comprises providing the plurality of individual structures such that the plurality of individual structures form a nonperiodic pattern.

3. The method according to claim 1, which comprises providing the plurality of individual structures such that the plurality of individual structures form a lattice having different periocticities along different directions.

4. The method according to claim 1, which comprises generating the reference signatures optically by measuring at least one of a diffraction and a scattering of an electromagnetic radiation at the structured surfaces.

5. The method according to claim 1, which comprises generating the at least one signature optically by measuring at least one of a diffraction and a scattering of an electromagnetic radiation at the plurality of individual structures of the test specimen surface to be monitored.

6. The method according to claim 1, which comprises classifying the test specimen surface by selectively classifying the test specimen surface as a good test specimen surface and a bad test specimen surface.

7. The method according to claim 1, which comprises providing a classification in accordance with graduated quality classes for classifying the test specimen surface.

8. The method according to claim 1, which comprise providing a classification in accordance with specific production faults for classifying the test specimen surface.

9. The method according to claim 1, which comprises monitoring a production of periodic memory element structures.

10. The method according to claim 1, which comprises monitoring a production of nonperiodic logic structures.

11. The method according to claim 1, wherein the step of providing the reference signatures includes producing a classification system by assigning given production prototypes having a specified quality to measurement data of the reference signatures of the given production prototypes.

12. The method according to claim 1, wherein the step of providing the reference signatures includes producing a classification system by assigning at least one of the production prototypes having the specified quality and measurement data of the reference signatures of the production prototypes to at least two classes.

13. The method according to claim 1, wherein the step of providing the reference signatures includes providing reference signatures for different products, and the step of classifying the parameters of the test specimen surface includes identifying a product.

14. The method according to claim 1, wherein the step of providing the reference signatures includes adjusting at least one of the production prototypes in different ways, and the step of classifying the parameters of the test specimen surface includes classifying a misadjustment of a test specimen.

15. The method according to claim 1, which comprises providing the structured surfaces as microstructured surfaces.

16. A device for monitoring fabrication processes of structured surfaces in a semiconductor production, comprising:

a reference signature apparatus for providing reference signatures of structured surfaces, said reference signature apparatus being configured for performing a measurement of reference signatures by measuring an intensity distribution of images varying at least a wavelength and a polarization of an electromagnetic radiation, the images being selected from the group consisting of diffraction images and scattered light images of a plurality of individual structures of a surface of production prototypes having a specified quality;

an apparatus for providing at least one of a neural network and a fuzzy logic having a learning capability by adjusting a weighting of the at least one of the neural network and the fuzzy logic as a function of the reference signatures;

a measuring apparatus operatively connected to said reference signature apparatus, said measuring apparatus measuring at least one signature associated with a test specimen surface to be monitored by simultaneously registering a plurality of individual structures of the test specimen surface to be monitored by using an intensity distribution of images varying at least a wavelength and a polarization of an electromagnetic radiation, the images being selected from the group consisting of diffraction images and scattered light images for providing a measured signature, measurements for both the reference signatures and the at least one signature of the test specimen surface to be monitored being performed one at a time;

a rotation apparatus for varying the polarization of the electromagnetic radiation by rotating an electromagnetic radiation source;

a comparison module operatively connected to said measuring apparatus, said comparison module comparing the measured signature with the reference signatures and providing comparison results by using at least one of the fuzzy logic and the neural network to evaluate similarity between the reference signatures and the measured signature;

a classification module operatively connected to said comparison module; and a high-resolution measuring device for measuring individual structures of the test specimen surface for providing absolute quantities of the individual structures on the surface with high resolution and for providing a further reference signature, the weighting of the at least one of the neural-network and the fuzzy logic being adjusted as a function of the further reference signature;

said classification module classifying parameters of the test specimen surface based on the comparison results, if a similarity between the reference signatures and measured signature has been found in the comparison step, otherwise classifying parameters of the test specimen surface based on the measurement of the individual structures.

17. The device according to claim 16, wherein said reference signature apparatus, said measuring apparatus, said comparison module, and said classification module are integrated in a semiconductor fabrication line for providing at least one of an in situ production monitoring and an in-line production monitoring.

18. The device according to claim 16, wherein:
said measuring apparatus includes an electromagnetic radiation source for providing a coherent electromagnetic radiation, a rotation apparatus for rotating a polarization of the coherent electromagnetic radiation, said rotation apparatus rotating the polarization in one of an infinitely adjustable manner and in small increments, and at least one electromagnetic radiation detector; and
said measuring apparatus is configured such that the coherent electromagnetic radiation hits a structured test specimen surface at a fixed angle of incidence, and such that one of a local distribution and an intensity distribution of a diffraction image generated by reflecting the coherent electromagnetic radiation at the structured test specimen surface is measured as a function of the polarization by using said at least one electromagnetic radiation detector.

19. The device according to claim 16, wherein said measuring apparatus includes an electromagnetic radiation source for providing an electromagnetic radiation with a given wavelength, the wavelength is selected such that dimensions of the individual structures of the test specimen surface are of a same order of magnitude as the given wavelength.

20. The device according to claim 16, wherein:
said electromagnetic radiation source provides the electromagnetic radiation with one of a plurality of wavelengths and a plurality of wave length ranges; and
said measuring apparatus carries out a measurement one at a time as a function of the one of the plurality of wavelengths and the plurality of wave length ranges.

21. The device according to claim 16, wherein said measuring apparatus includes a spectral lamp for providing coherent light and filters for extracting various wavelength ranges from the coherent light.

22. The device according to claim 16, wherein:
said rotation apparatus rotates the polarization in one of an infinitely adjustable manner and in small increments, and said rotation apparatus is an element selected from the group consisting of a $\lambda/2$ plate, two $\lambda/4$ plates, an electro-optical element, and a mechanical rotating apparatus for mechanically rotating said electromagnetic radiation source.

23. The device according to claim 16, including a movable mounting table for holding a test specimen when measuring at least one distribution selected from the group consisting of a local distribution and an intensity distribution of diffraction images in various regions of the test specimen.

24. The device according to claim 16, wherein said measuring apparatus is moved with respect to a test specimen when measuring at least one distribution selected from the group consisting of a local distribution and an intensity distribution of diffraction images in various regions of the test specimen.

25. The device according to claim 16, wherein said measuring apparatus examines an electromagnetic radiation reflected by the test specimen surface to be monitored.

26. The device according to claim 16, wherein said classification module includes a diffraction simulator for determining absolute profile parameters from measured signatures.

* * * * *